United States Patent [19]

Boaz

[11] Patent Number: 5,126,267
[45] Date of Patent: Jun. 30, 1992

[54] PROTECTED HYDROXY METHOD FOR ALCOHOL-ESTER SEPARATION

[75] Inventor: Neil W. Boaz, Waterloo, N.Y.

[73] Assignee: Eastman Kodak Company, Rochester, N.Y.

[21] Appl. No.: 660,837

[22] Filed: Feb. 26, 1991

Related U.S. Application Data

[63] Continuation-in-part of Ser. No. 501,570, Mar. 30, 1990, abandoned.

[51] Int. Cl.⁵ .............. C12P 41/00; C07C 309/68; C07C 33/03
[52] U.S. Cl. .................. 435/280; 558/51; 558/52; 568/857; 568/868; 435/130; 435/157; 435/158
[58] Field of Search .............. 435/280, 130, 157, 158; 558/51, 52; 568/868, 857

[56] References Cited

U.S. PATENT DOCUMENTS

| | | | |
|---|---|---|---|
| 4,732,853 | 3/1988 | Whitesides et al. | 435/123 |
| 4,745,066 | 5/1988 | Hamaguchi et al. | 435/130 |
| 4,863,859 | 9/1989 | Hamaguchi et al. | 435/280 |
| 4,865,771 | 9/1989 | Francalanci et al. | 562/567 |
| 4,921,798 | 5/1990 | Boaz | 435/146 |
| 4,923,810 | 5/1990 | Walts et al. | 435/117 |
| 4,971,909 | 11/1990 | Kaneoya et al. | 435/280 |
| 4,985,365 | 1/1991 | Mitsuda et al. | 435/280 |
| 4,996,158 | 2/1991 | Oda et al. | 435/280 |

*Primary Examiner*—Carolyn Elmore
*Attorney, Agent, or Firm*—J. Jeffrey Hawley

[57] ABSTRACT

A process is disclosed for the isolation of an enantiomerically enriched alcohol from a first mixture of an enantiomerically enriched alcohol and an enantiomerically enriched ester. The process includes the steps of:

(a) contacting the mixture with a reagent capable of reacting with the hydroxy function of the alcohol, without the loss of optical purity, so as to produce a second mixture containing a base stable derivative of the enantiomerically enriched alcohol and the unreacted ester;

(b) contacting the second mixture with a base capable of reacting with the ester so as to produce a third mixture containing a compound more volatile than the base stable derivative of the alcohol;

(c) removing the volatile compound from the third mixture; and (d) converting the base stable derivative of the alcohol back to the enantiomerically enriched alcohol, without the loss of optical purity.

9 Claims, No Drawings

PROTECTED HYDROXY METHOD FOR ALCOHOL-ESTER SEPARATION

CROSS REFERENCE TO RELATED APPLICATIONS

The present application is a continuation-in-part of U.S. Ser. No. 501,570, filed Mar. 30, 1990, entitled METHOD FOR THE PREPARATION OF OPTICALLY ACTIVE α, β-UNSATURATED EPOXIDES in the names of Boaz and Laumen. That parent application was abandoned as of the filing date accorded this application.

Reference is made to the following copending and commonly assigned applications, filed on even date herewith by Neil W. Boaz:

U.S. Ser. No. 660,838, entitled ALCOHOL-ESTER SEPARATION BY REACTION WITH BICARBONATE IN POLYHYDROXY SOLVENT, U.S. Ser. No. 660,839, entitled ALCOHOL-ESTER SEPARATION BY REACTION WITH ACETATE, and U.S. Ser. No. 660,830, entitled ALCOHOL-ESTER SEPARATION BY RECRYSTALLIZATION.

FIELD OF THE INVENTION

The present invention relates to a process for producing enantiomerically enriched compounds from a mixture which can be derived from the enzymatic enantioselective hydrolysis of a racemic ester or the enzymatic enantioselective esterification of a racemic alcohol. The resulting enantiomerically enriched compounds find a number of uses as starting materials for other compounds. Some of the compounds are useful, for example, for the production of 2-deoxy-Dribose. Other compounds are useful in the preparation of leukotrienes.

BACKGROUND OF THE INVENTION

Chemoenzymatic synthesis is a preparative strategy which employs both chemical and biocatalytic steps in a reaction sequence. The biocatalytic transformations convert one organic compound to another by the use of enzymes, either isolated or as part of biological systems. These biocatalysts (enzymes) are in principle the same as any other type of catalyst. However, there are circumstances where these biocatalysts are especially useful, such as the induction of chirality due to enzyme enantiospecificity. These enzymatic reactions occur under mild conditions and are often more environmentally acceptable than classical chemical processes.

Lipases are the closest to optimum biocatalysts. They are isolated extracellular enzymes whose natural function is to hydrolyze glycerol esters. Many have wide substrate acceptability for ester hydrolysis, or, under the correct conditions, alcohol esterification. They are readily (and often cheaply) available and are experimentally simple, requiring no added cofactors and affording no side products. Not surprisingly these enzymes have been the most thoroughly studied for biocatalytic use in organic chemistry.

There are two types of substrate classes for lipase-catalyzed reactions. Meso or prochiral substrates constitute the first and most widelystudied class. The inherent chirality of the lipase distinguishes between two prochiral functions (esters or alcohols) on the same molecule to afford 100% conversion to (optimally) a single enantiomer.

The second class of substrates are the racemic systems, in which (optimally) only one of two enantiomers is recognized and hydrolyzed (or esterified) by the lipase, affording a 50% conversion to product and 50% recovered starting material of opposite configurations. This mixture must be physically separated to complete the enantiomeric differentiation. For substrates in which the acid rather than the alcohol portion is of interest, the separation is often possible by simple aqueous base extraction.

Alcohol-based substrates pose the most challenging separation problems due to the gross physical similarity between the alcohol and ester. It is to separations of this type that the present invention is directed.

Chemoenzymatic synthesis of optically active epoxybutadiene (hereinafter EpB) is a potentially attractive preparative method since a readily available source of EpB has recently become available. Novel, simple, and efficient preparations of optically pure C4 synthons derived from EpB would be synthetically useful, since most currently available chiral synthons have a three- or five-carbon backbone due to availability from natural sources. In fact, chain elongation of C3 synthons from the chiral pool currently comprises the major method for the preparation of optically active EpB and the corresponding diol (1,2-dihydroxy-3-butene).

For example, an early route to S-1,2-dihydroxy-3-butene and S-EpB relied on C6 D-mannitol (two identical three-carbon pieces) as the chiral starting material. (Baer, E.; Fischer, H. O. L. J. Biol. Chem. 1939, 128, 463) After formation of the terminal (symmetrical) diacetonide, the vicinal diol was oxidatively cleaved with lead tetraacetate to provide two molecules of the unstable acetonide of the three-carbon synthon R-glyceraldehyde. Wittig reaction with methylene triphenylphosphorane afforded 1,2-dihydroxybutene acetonide which was readily deprotected to the optically active 1,2-dihydroxybutene. Monotosylation of the diol and base treatment afforded optically active EpB. (Crawford, R. J.; Lutener, S. B.; Cockcroft, R. D. Can. J. Chem. 1976, 54, 3364.)

The corresponding R enantiomers were available from the antipodal three carbon synthon S-glyceraldehyde acetonide which has been prepared from L-ascorbic acid by several routes. After initial differential protection of the hydroxyl groups by sequential actonide formation and methylation, ozonolysis and lithium aluminum hydride treatment afforded S,S-1,2,3,4-tetrahydroxybutane 1,2-acetonide. Lead tetraacetate oxidative cleavage resulted in the desired S-glyceraldehyde acetonide. This material can be transformed to optically active R-1,2-dihydroxy-3-butene and ultimately to R-EpB.

Alternatively, optically active 1,2-dihydroxy-3-butene can be prepared from one of the few four carbon synthons available from the chiral pool, tartaric acid. After preparation of the acetonide and reduction of the carboxyl groups, formic acid-induced rearrangement and hydrolysis of the resulting formates afforded the desired diol. This can be transformed to optically active EpB.

All routes suffer from synthetic problems. The oxidation steps mentioned above can be troublesome and produce highly toxic (lead) by-products. The first two routes also involve a cumbersome Wittig olefination of glyceraldehyde acetonide, itself a rather unstable species. In addition, each of the two routes can only be utilized for a single (but complementary) enantiomer due to the commercial availability of only D-mannitol and L-ascorbic acid. The route from tartaric acid is complicated by the formation of 1,4-dihydroxy-2-butene during the rearrangement reaction. Separation of this isomer from the desired 1,2-dihydroxy-3-butene is not trivial.

In actuality, only the route from tartaric acid is directed towards C4 synthons. The other schemes afford C4 materials as an afterthought by chain extension. A more direct approach, the synthesis of optically active C4 synthons from corresponding racemic C4 starting materials, would afford greater versatility for the preparation of diverse organic molecules. Therefore, the preparation of optically active EpB and derivatives (from racemic EpB) using biocatalysis technology is of great interest. An enantioselective lipase-catalyzed hydrolytic approach to this problem seemed promising due to the presence of diverse oxygen functionalities in many EpB derivatives.

EpB can be converted to a racemic ester by a number of routes. This ester is then subjected to enzymatic enantioselective hydrolysis to produce a mixture of enantiomerically enriched alcohol and ester. While these compounds can be separated using chromatographic separation techniques, this is not practical on a large scale. Unfortunately, as mentioned previously, the separation of the alcohol from the ester is difficult because of the similarity of the physical characteristics of these compounds.

Thus, the present invention is directed to the problem of separating an optically active alcohol from a related optically active ester.

SUMMARY OF THE INVENTION

In accordance with the present invention, there is provided a process for the isolation of an enantiomerically enriched alcohol from a first mixture of an enantiomerically enriched alcohol and an enantiomerically enriched ester, said process comprising the steps of:

(a) contacting said mixture with a reagent capable of reacting with the hydroxy function of said alcohol, without the loss of optical purity, so as to produce a second mixture containing a base-stable derivative of said enantiomerically enriched alcohol and the unreacted ester;

(b) contacting said second mixture with a base capable of reacting with said ester so as to produce a third mixture containing a compound more volatile than said base-stable derivative of said alcohol;

(c) removing said volatile compound from said third mixture; and (d) converting said base-stable derivative of said alcohol back to said enantiomerically enriched alcohol, without the loss of optical purity.

The invention is particularly useful in separating the alcohol and ester that are formed by the enzymatic enantioselective hydrolysis of a racemic acetate or the enzymatic enantioselective esterification of a racemic alcohol, with the racemic acetate or alcohol each in turn formed from 3,4-epoxy-1-butene. Thus, the invention is particularly useful for the isolation of an enantiomerically enriched 1-arylsulfonate-2-hydroxy-3-butene from a mixture containing the 1-arylsulfonate-2-hydroxy-3-butene and a 1-arylsulfonate-2-acyloxy-3-butene.

DETAILED DESCRIPTION OF THE INVENTION

In preferred embodiments, the mixture is represented by:

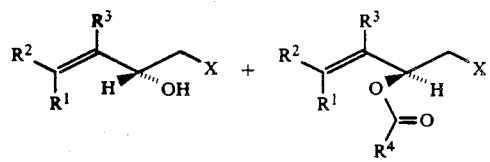

wherein each R is a group stable to nucleophilio, basic, and mildly acidic conditions and is independently selected from H, straight- or branched-chain substituted or unsubstituted alkyl, aryl, substituted aryl, arylalkyl, non-nitrogen-containing heteroaryl or substituted heteroaryl, or halogen. Substituents as designated above can be chosen from halogen, alkoxy, aryloxy, cyano, arylthio, alkylthio.

X is selected from halogen (F, Cl, Br, I) or sulfonate esters such as p-toluenesulfonate, phenylsulfonate, p-bromobenzenesulfonate, 4-chloro-3-nitrobenzenesulfonate, 2,5-dichlorobenzenesulfonate, 5-dimethylamino-1-naphthalenesulfonate, 2,4-dinitrobenzenesulfonate, p-iodobenzenesulfonate, 1-naphthalenesulfonate, 2-naphthalenesulfonate, o-nitrobenzenesulfonate, m-nitrobenzenesulfonate, p-nitrobenzenesulfonate, 2-thiophenesulfonate, methanesulfonate, trifluoromethanesulfonate, and the like.

In the first step of the process of the invention, the mixture is reacted with reagents that react with the hydroxy function of the alcohol of the mixture so as to protect the hydroxy group, without the loss of optical purity, thereby producing a basestable derivative. The protecting group attached in this first step is a base-stable protecting group such as a 2-tetrahydropyranyl group, a 1-ethoxyethyl group, a methoxymethyl group, a methylthiomethyl group, a benzyloxymethyl group, a t-butoxymethyl group, a 2-methoxyethoxymethyl group, a 2,2,2-trichloroethoxy methyl group, a bis(2-chloroethoxy)methyl group, a 2-(trimethylsilyl)ethoxymethyl group, a 2-(3-bromotetrahydropyranyl) group, a 2-tetrahydrothiopyranyl group, a 4-(4-methoxytetrahydropyranyl) group, a 4-(4-methoxytetrahydrothiopyranyl) group, a 4-(4-methoxytetrahydrothiopyranyl)-S,S-dioxide group, a 2-tetrahydrofuranyl group, a 1-(1-methyl-1-methoxyethyl) group, or a 1-(1-isopropoxyethyl) group. The preferred reagent is dihydropyran so as to produce a 2-tetrahydropyranyl protecting group.

The reaction to form the protected alcohol is performed under conditions such that the alcohol is protected without the loss of optical purity. Where the protecting group is attached to the alcohol by a displacement reaction, typical reaction conditions comprise mild heating of the reaction mixture comprising the 1-arylsulfonate-2-hydroxy-3-butene and at least an equimolar amount (with substantial excess acceptable) of the protecting group precursor in the presence of one or more equivalents of a nonnucleophilic base. Reaction temperatures in the range of about 25° C. up to about 100° C. are typically employed. Conditions to be avoided include strong acid conditions, e.g., a pH of about 0, which could lead to the cleavage of the allylic carbon-oxygen bond.

Where the protecting group is incorporated by olefin addition, typical reaction conditions comprise contacting the compound to be protected and at least an equimolar amount (with substantial excess acceptable) of the precursor of the hydroxy protecting group in the presence of a catalytic quantity of a moderate to strong organic or inorganic acid or salt thereof in an aprotic solvent (e.g., cyclic and acyclic ethers, halogenated hydrocarbons, aromatic hydrocarbons, etc.)

In the second step of the process of the invention, the mixture that is formed in the first step, containing the protected alcohol and the ester, is contacted with base that is capable of reacting with the ester to produce a more volatile material that can be removed in subsequent steps of the process. For example, 1-tosyloxy-2-acetoxy-3-butene can be converted to epoxybutadiene by treatment with potassium carbonate and ethylene glycol. This epoxybutadiene is considerably more volatile that the protected alcohol and can be easily removed in the third step of the process by distillation.

Useful bases for this second step of the process include metal hydroxides of the structural formulae: MOH or M'(OH)2 wherein M is an alkali metal and M' is an alkaline earth metal; or metal carbonates of the structural formulae M2(CO3), MH(CO3) and M'(CO3) wherein M and M' are defined above.

Especially preferred bases for use in the invention are alkali metal carbonates, e.g., potassium carbonate.

Forming of the epoxide, e.g. EpB, from the ester is carried out by contacting the mixture with base, as indicated. Typical conditions include a reaction temperature in the range of about −20° C. up to about 150° C. The ratio of base to ester is about equimolar or greater. The reaction can optionally be carried out in the presence of a suitable solvent such as a poly-hydroxy containing solvent having about 2 to 4 carbon atoms. As indicated above, a preferred solvent is ethylene glycol.

In the last step of the process, the protected alcohol can be converted back to the alcohol by acid hydrolysis. Acid hydrolysis conditions sufficient to remove base-stable hydroxy protecting groups typically comprise contacting the protected alcohol with at least a catalytic amount of an organic acid, a mineral acid or a Lewis acid, or salt thereof, in a protic solvent at a temperature in the range of about 25° C. up to about 100° C. for a time sufficient to substantially completely deprotect the alcohol. This is typically in the range of about 0.5 up to about 48 hours. The resulting hydroxytosylate can be purified by recrystallization to substantial optical purity.

Thus, the process of the invention can be illustrated, in its preferred embodiment, by the following reaction scheme:

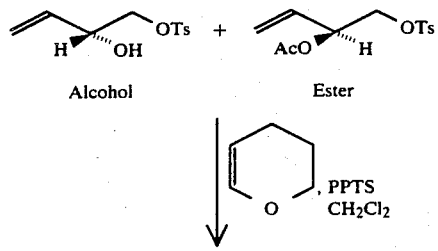

Alcohol     Ester

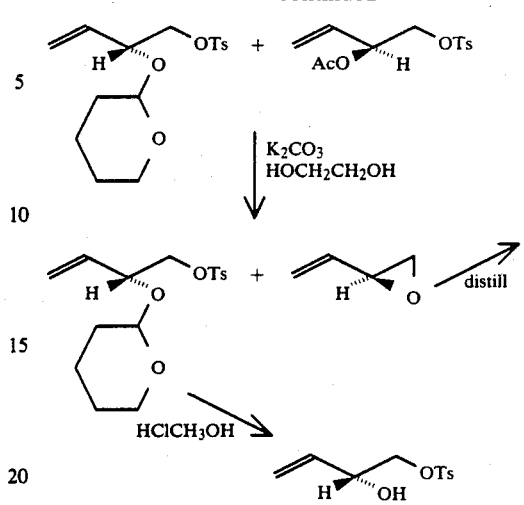

The invention relates to a method for the separation of an optically active alcohol from an optically active ester. The preparation of a typical mixture of this type will be discussed. In this process, EpB is first converted to a racemic acetate. This acetate is then subjected to enzymatic hydrolysis to produce the desired starting mixture. It will be understood, however, that the method of obtaining the desired mixture as well as the particular mixture itself or the proportions thereof is not critical to the invention in its broadest aspect. The described route is merely a preferred route.

A useful racemic ester starting substrate for enzymatic hydrolysis can be prepared from EpB by two routes. For efficiency, a tosylate group was chosen as the 1-alkoxy substituent to allow ready intramolecular displacement to form the optically active EpB. In addition, enzymatic hydrolysis of tosylated glycerol derivatives has been reported. (Hamaguchi, S.; Ohashi, T.; Watanabe, K. Agric. Biol. Chem. 1986, 50, 1629.) Groups other than tosylate can be used when other considerations become more important.

The 1-tosyloxy-2-acetoxy-3-butene substrate is also preferred since it can be hydrolyzed with high R-enantioselectivity by common lipases, affording a rapid route to optically active EpB.

The racemic acetate substrate was prepared by one of two methods. The diol route began with racemic 1,2-dihydroxy-3-butene which could be prepared by reacting EpB with water under neutral conditions or with acid catalysis. The diol was treated with p-toluenesulfonyl chloride (p-TsCl) in pyridine at 4° C. to afford the desired monotosylate contaminated with about 10% of the corresponding ditosylate. The monotosylate could be selectively crystallized to afford pure monotosylate in 61% yield. Hydroxytosylate was acetylated under normal conditions (Ac2O, Et3N, CH2Cl2) to provide the acetoxy-tosylate (the desired racemic acetate) in 93% yield. The diol route is illustrated as follows:

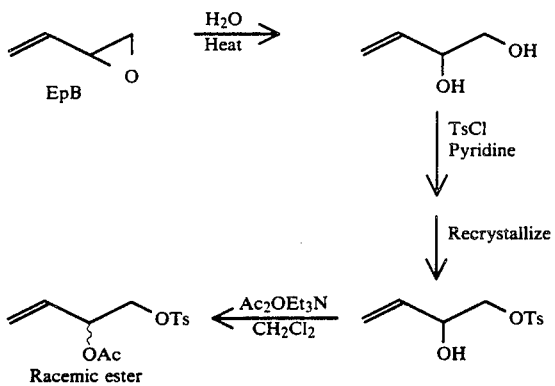

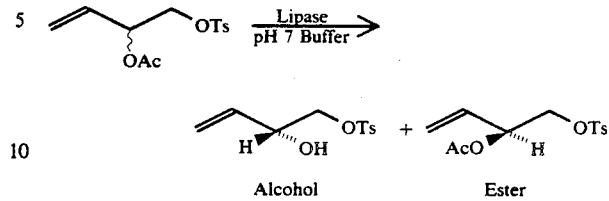

Alternatively, the acetoxy-tosylate could be prepared by initial reaction of EpB with acetic acid under palladium(0) catalysis to afford 1-hydroxy-2-acetoxy-3-butene. Tosylation under normal conditions (p-TsCl, Et3N, CH2Cl2, 88%) afforded the desired product. However, the isomeric inconsistency of the monoacetate material (acetyl migration during distillative purification) and the inseparability of the positional isomers of two intermediates posed significant problems, since the unwanted isomers complicated the enzymatic hydrolysis. Therefore, the former (diol) preparation is preferred.

In the next step, the racemic ester was hydrolyzed in the presence of a lipase. (Convenient lipases are Lipase SAM-II ® derived from *Pseudomonas fluorescens* and Lipase PS-30 ® derived from *Pseudomonas cepacia*, both commercially available from Amano International Enzyme Company.)

The enzymatic enantioselective hydrolysis of the racemic ester proceeds using only a small amount (e.g., 50 mg crude lipase/0.1 mol racemic ester) of the lipase from *Pseudomonas fluorescens* or from *Pseudomonas cepacia*. The reaction can be performed as an emulsion in aqueous pH 7 phosphate buffer under automatic titration conditions ("pH Stat", end point pH 7.00), allowing the reaction to be followed by the uptake of 1.000 N NaOH. The reaction can be stopped at about 50% conversion, affording the R-enantiomer of the optically active alcohol and unreacted S-ester. The R-selectivity of the hydrolysis is very high, affording both enantiomers in high optical purity [both >80% enantiomeric excess (ee)]with an R to S hydrolysis rate ratio (E value) of between 200 and 300. This is what is meant by "enantiomerically enriched". (The E value is determined in accordance with the methods described in (a) Chen, C. S.; Fujimoto, Y.; Girdaukas, G.; Sih, C. J. *J. Am. Chem. Soc.* 1982, 104, 7294. or (b) Chen, C. S.; Wu, S. H.; Girdaukas, G.; Sih, C. J. *J. Am. Chem. Soc.* 1987, 109, 2812.) In the same manner, "substantially optically pure" means >98% ee.

Alternatively, the lipase isolated from *Pseudomonas Novo* sp. ATCC 21808 can be used, affording the same configurational selectivity with an E value of upwards of 300.

A solution or well-dispersed emulsion is important for the success of an enzymatic hydrolysis reaction. In certain instances the mixture of optically active alcohol and optically active ester formed an undesirable gel prior to completion of the hydrolysis, halting the reaction early. A 9:1 pH 7 Buffer:tetrahydrofuran solvent mixture avoided this problem and also afforded a more rapid hydrolysis reaction (rate increased by a factor of 2) without sacrificing enantioselectivity (E values of up to 254 were observed). The enzymatic hydrolysis is illustrated as follows:

Substrate Preparation and Enzymatic Hydrolysis Diol Preparation

Addition of Water to EpB

EpB (250g) was added to 800 mL of water, followed by 10 g of an acid resin. The reaction mixture was stirred at room temperature overnight. The catalyst was removed by filtration and the filtrate was concentrated at reduced pressure. Distillation of the residue (60-65° C./1 mm) provided 3,4-dihydroxy-but-1-ene in 85% yield. $^1$H NMR (CDCl3): 5.9 (m, 1H); 5.4-5.2 (m, 2H); 4.25 (m 1H); 3.7 (m, 1H); 3.5 (m, 1H); 2.3 (br s, 1H). Ir(CCl4): 3600, 3499 (broad), 2900, 2880 cm$^{-1}$. Ms: 87, 70, 57, 42, 31, 29 m/e.

1-Tosyloxy-2-hydroxy-3-butene (Racemic Ester. diol route)

1,2-Dihydroxy-3-butene (20.00 g; 0.227 mol; 1.05 equiv) was dissolved in pyridine (200 mL). The reaction mixture was cooled in an ice bath and p-toluenesulfonyl chloride (p-TsCl) (41.11 g; 0.216 mol) was added in four portions over 30 min. After thorough mixing, the reaction mixture was placed at 4° C. for 18 h, at which time thin layer chromatography (hereinafter TLC) analysis indicated no p-TsCl. The mixture was concentrated to about half the original volume at reduced pressure from a 40° C. water bath and then diluted with ether (200 mL). The mixture was washed with water (100 mL), ice-cold 3 N HCl until the washes remained acidic (2×100 mL), and saturated sodium bicarbonate (100 mL). After drying the organic solution (MgSO4), the solvent was removed to afford 41.73 g of a 91:9 mixture ($^1$H nmr analysis) of the desired compound and the corresponding di-tosylate. The crude product solidified over several days at −20° C. It was recrystallized from methylene chloride (50 mL) by the addition of hexanes (100 mL) and chilling to -20° C. to afford two crops (total 33.33 g; 61%) of the desired compound which was pure by TLC analysis, mp 38°-44° C. 1H nmr (300 MHz, CDCl3): 7.800 (2H, d, J=8.25 Hz); 7.356 (2H, d, J=8.19 Hz); 5.751 (1H, ddd, J=5.38, 10.46, 16.55 Hz); 5.378 (1H, br d, J=17.05 Hz); 5.247 (1H, br d, J=10.48 Hz); 4.396 (1H, m); 4.066 (1H, dd, J=3.39, 10.20 Hz); 3.906 (1H, dd, J=7.41, 10.22 Hz); 2.451 (3H, s); 2.276 (1H, d, J=4.50 Hz). IR (KBr, cm$^{-1}$): 3520 (s,b); 1650 (w); 1600 (s); 1350 (s); 1170 (s). Combustion Analysis: Theor - C, 54.53; H,5.82; N, 0. Found - C, 54.84; H, 5.86; N, <0.3.

1-Tosyloxy-2-acetoxy-3-butene

Tosylate from above (25.00 g; 0.103 mol) was dissolved in methylene chloride (125 mL) and cooled to 0° C. Triethylamine (21.5 mL; 0.155 mol; 1.5 equiv) was added followed dropwise by acetic anhydride (11.7 mL;

0.124 mol; 1.2 equiv). The reaction mixture was allowed to warm to room temperature and after 2.5 days no starting tosylate was visible by TLC analysis. The mixture was poured into ether (250 mL), washed with water (2×50 mL) and saturated sodium bicarbonate (50 mL), dried (MgSO4), and concentrated. The crude product was stirred with pH 7 phosphate buffer (100 mL) for 1.5 h to hydrolyze any excess acetic anhydride and extracted with ether (3x50 mL). The combined ether extracts were dried (MgSO4) and concentrated to afford 27.51 g (93%) of acetate product. 1H nmr (300 MHz, CDC13): 7.786 (2H, d,J=8.26 Hz); 7.355 (2H, d, J=8.03 Hz); 5.710 (1H, ddd, J=6.23, 10.54, 17.05 Hz); 5.396 (1H, m); 5.324 (1H, d, J=16.72 Hz); 5.279 (1H, d, J=10.63 Hz); 4.09 (2H, m); 2.453 (3H, s); 2.017 (3H, s). IR (neat film, cm$^{-1}$): 1740 (s); 1645 (w); 1600 (m); 1360 (s); 1175 (s).

Optically active R-(+)-alcohol ([$\alpha$]$D^{20}$+7.14°(c. 1.036, methanol)) afforded R-(+)-ester, [$\alpha$]$D^{20}$+5.30° (c. 1.246, methanol), by this methodology.

Enzymatic Enantioselective Hydrolysis of Racemic Ester using SAM-II

Racemic ester described above (25.76 g; 90.6 mmol) and pH 7 phosphate buffer (90 g) were combined and vigorously stirred under pH Stat conditions (automatic titration - pH 7.00 end point). Once the pH had stabilized at 7.00, the lipase from *Pseudomonas fluorescens* *(SAM II)* (50 mg) was added. The mixture was stirred for 15 h under pH Stat conditions at which time 45.54 mL of 1.000 N NaOH had been consumed. The mixture was extracted with methylene chloride (3×100 mL), dried (Na2SO4), and concentrated to afford 23.47 g (98% material recovery) of the mixture of alcohol and ester. A portion (about 350 mg) was flash chromatographed (elution with 1:2 ethyl acetate:hexanes) to afford R-alcohol (148 mg; 92% ee) and S-ester (195 mg; 94% ee). Enantiomeric excess was determined using a method analogous to that described in Dale et al, J. Org. Chem., 1969, Vol 33, p2543.

R-alcohol: [$\alpha$]$D^{20}$+7.14° (c. 1.036, methanol).
S-ester: [$\alpha$]$D^{20}$−5.29° (c. 1.324, methanol).
All other properties are as described above for the alcohol and the ester.

Enzymatic Enantioselective Hydrolysis of Racemic Ester using the lipase from Pseudomonas Novo Sp. ATCC 21808

Racemic ester prepared as above (1.42 g; 5.00 mmol) and pH 7 phosphate buffer (20 g) were combined and vigorously stirred under pH Stat (automatic titration - pH 7.00 end point) conditions. Once the pH had stabilized at 7.00, an ammonium sulfate suspension of the lipase from *Pseudomonas novo* Sp. ATCC 21808 (1.00 mL) was added. The mixture was stirred for 4 h under pH Stat conditions at which time 2.471 mL of 1.000 N NaOH had been consumed (49.4 % conversion). The mixture was extracted with methylene chloride (3×20 mL), dried (MgSO4), and concentrated. The crude product was flash chromatographed using 3:1 hexanes::ethyl acetate as eluent to afford 670 mg (47%; 92% ee) of S-ester and 447 mg (37%; 98% ee) of R-alcohol (one overlap fraction). Enantiomeric excess was determined using a method analogous to that described in Dale et al, J. Org. Chem., 1969, Vol 33, p2543.

R-alcohol: [$\alpha$]$D^{20}$+7.14° (c. 1.036, methanol).
S-ester: [$\alpha$]$D^{20}$−5.29° (c. 1.324, methanol).

All properties of the alcohol and the ester are as reported above.

Reduction of the olefin of the R-alcohol afforded the corresponding (−)-1,2-butanediol monotosylate. This compound is known to possess the R-(−) configuration (Hamaguchi, et al, Agri. Biol. Chem. vol 50, pg 1629 (1986).

The following example is submitted for a further understanding of the invention:

EXAMPLE 1

Preparation of a Mixture of R-1-Tosyloxy-2-(2-tetrahydropyranyloxy)-3-butene and S-1-Tosyloxy-2-acetoxy-3-butene

Method A

A 1:1 mixture of R-1-tosyloxy-2-hydroxy-3-butene and S-1-tosyloxy-2-acetoxy-3-butene (23.01 g; 43.7 mmol each) from the enzymatic hydrolysis was dissolved in methylene chloride (125 mL). Dihydropyran (7.89 mL; 87.4 mmol; 2 equiv) was added and the reaction mixture was stirred for 1.5 h at room temperature at which time TLC analysis indicated no alcohol. After concentration, TLC analysis indicated partial reversion to the alcohol, so the crude product was resubmitted to the above conditions. After 2 h, no alcohol was observed by TLC. The reaction mixture was diluted with ether (200 mL), washed with water (50 mL), dried (MgSO4), and concentrated to afford 28.82 g (108%) of a mixture of R-1-tosyloxy-2-(2-tetrahydropyranyloxy)-3-butene and unchanged ester (with a small amount of by-product).

Method B

A 1:1 mixture of the alcohol and the ester (275 mg; 0.523 mmol each) from the enzymatic hydrolysis was dissolved in ether (2.5 mL). Dihydropyran (95 μL; 1.046 mmol; 2 equiv) was added followed by about 1 mg (about 0.01 equiv) of pyridinium p-toluenesulfonate (PPTS). The reaction mixture was stirred at room temperature until TLC analysis indicated complete consumption of the alcohol (overnight). The reaction mixture was diluted with ether (10 mL), washed with saturated NaHCO3 (2x5 mL), dried (MgSO4), and concentrated to afford 326 mg (102 %) of a mixture of R-1-tosyloxy-2-(2-tetrahydropyranyloxy)-3-butene and S-1-tosyloxy-2-acetoxy-3-butene, pure by TLC and 1H nmr analysis. R-1-tosyloxy-2-(2-tetrahydropyranyloxy)-3-butene: $^1$H nmr (300 MHz, CDC13): 7.802, 7.781 (2H, 2xd,. J=8.17 Hz; J'=7.95 Hz); 7.337 (2H, d, J=8.03 Hz); 5.751, 5.588 (1H, 2xddd, J=7.09, 10.13, 17.34 Hz); 5.375–5.190 (2H, m); 4.724, 4.650 (1H, 2xt, J=3.15 Hz; J'=3.05 Hz); 4.336 (1H, br q, J=6.36 Hz); 4.02 (2H, m); 3.83 (1H, m); 3.43 (1H, m); 2.445 (3H, s); 1.8–1.4 (6H, m). IR (neat film, cm−1): 1600 (m); 1360 (s); 1175 (s). All properties of 1-tosyloxy-2-acetoxy-3-butene are as described above.

S-1-Epoxy-3-butene (S-EpB).
R-1-Tosyloxy-2-(2-tetrahydropyranyloxy)-3-butene The 1:1 mixture of tetrahydropyran ether and acetate (6.95 g; 11.4 mmol each) as prepared above was partially dissolved in ethylene glycol (22 mL) and any volatiles were removed in vacuo. Potassium carbonate (1.89 g; 13.7 mmol; 1.2 equiv) was added and the reaction vessel was sealed and stirred at room temperature for 1.5 h to completely consume the acetate (TLC analysis). S-EpB was then distilled directly from the reaction mixture at about 5 mm Hg at room temperature and collected in a receiver cooled to −78° C. The co-distilled water layer was physically removed to afford 439 mg (55%; 26% overall yield from racemic ester) of S-EpB which was spectroscopically identical with authentic (racemic) EpB. The residual reaction mixture was diluted with ether (50 mL), washed with water (3×30 mL), dried (MgSO4), and concentrated to afford 3.71 g (100%; 50% from racemic ester) of R-1-tosyloxy-2-(2-tetrahydropyranyloxy)-3-butene. S-EpB: $^1$H nmr (300 MHz, CDC13): 5.522 (2H, m); 5.298 (2H, m); 3.345 (1H, quintet, J=3.15 Hz); 2.967 (1H, t, J=4.43 Hz); 2.657 ($^1$H, dd, J=2.31, 5.17 Hz).[α]D$^{20}$+20.2° (c. 0.872, pentane). All properties of R-1-tosyloxy-2-(2-tetrahydropyranyloxy)-3-butene are as described above.

Hydrolysis of THP ether to regenerate Alcohol

THP ether (3.36 g; 10.3 mmol) recovered above was dissolved in methanol (15 mL) and concentrated hydrochloric acid (5 drops; cat.) was added. The reaction mixture was stirred at room temperature for 1.5 h, at which time TLC analysis indicated no residual R-1-tosyloxy-2-(2-tetrahydropyranyloxy)-3butene. The reaction mixture was diluted with ether (75 mL), washed with saturated NaHCO3 (2×20 mL), dried (MgSO4), and concentrated to afford 2.71 g (110%; 55% overall from racemic ester) of the alcohol R-1-tosyloxy-2-(2-hydroxy)-3-butene (ca. 92% ee) along with a small amount of dihydropyran-derived byproduct. The alcohol can be recrystallized at this point by dissolving it in ether (5 mL/g), adding hexanes (10 mL/g) and standing at room temperature. A single recrystallization removes impurities and affords substantially optically pure alcohol, mp 59°-60° C., in about 35°-40% overall yield from racemic ester. All achiral properties of R-1-tosyloxy-2-(2-hydroxy)-3-butene are as described above.- [α]D$^{20}$+7.98° (c. 1.04, methanol)

The present invention has been described with reference to particularly preferred embodiments thereof. However, it will be understood that modifications and extensions can be effected within the spirit and scope of the invention.

We claim:

1. A process for the isolation of an enantiomerically enriched alcohol from a first mixture of an enantiomerically enriched alcohol and an enantiomerically enriched ester, wherein said mixture is represented by the structures:

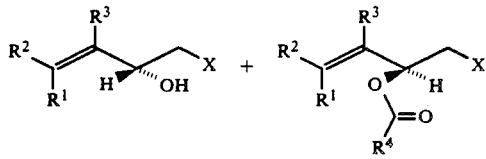

wherein $R^1$, $R^2$ and $R^3$ are a group stable to nucleophilic, basic, and acidic conditions and is independently selected from H, straight- or branched-chain substituted or unsubstituted alkyl, aryl, substituted aryl, arylalkyl, non-nitrogen-containing heteroaryl or substituted heteroaryl, or halogen; $R^4$ is selected from H, straight- or branched chain substituted or unsubstituted alkyl, aryl, substituted aryl, arylalkyl, non-nitrogen containing heteroaryl or substituted heteraryl;

X is selected from halogen or sulfonate esters; said process comprising the steps of:

(a) contacting said mixture with a reagent capable of reacting with the hydroxy function of said alcohol, without the loss of optical purity, so as to produce a second mixture containing a base-stable derivative of said enantiomerically enriched alcohol and the unreacted ester;

(b) contacting said second mixture with a base capable of reacting with said ester so as to produce a third mixture containing an epoxide compound more volatile than said base-stable derivative of said alcohol;

(c) removing said volatile compound from said third mixture; and (d) converting said base-stable derivative of said alcohol back to said enantiomerically enriched alcohol, without the loss of optical purity.

2. The process according to claim 1 wherein said sulfonate esters are selected from the group consisting of p-toluenesulfonate, phenylsulfonate, p-bromobenzenesulfonate, 4-chloro-3-nitrobenzenesulfonate, 2,5-dichlorobenzenesulfonate, 5-dimethylamino-1-naphthalenesulfonate, 2,4-dinitrobenzenesulfonate, p-iodobenzenesulfonate, 1-naphthalenesulfonate, 2-naphthalenesulfonate, o-nitrobenzenesulfonate, m-nitrobenzenesulfonate, p-nitrobenzenesulfonate, 2-thiophenesulfonate, methanesulfonate and trifluoromethanesulfonate.

3. A process according to claim 1 wherein said first mixture is produced by the enzymatic enantioselective hydrolysis of a racemic ester.

4. The process according to claim 3 wherein said racemic ester is derived from epoxybutadiene.

5. A process according to claim 1 wherein said reagent capable of reacting with the hydroxy function of said alcohol results in a protecting group selected from the group consisting of a 2-tetrahydropyranyl group, a 1-ethoxyethyl group, a methoxymethyl group, a methylthiomethyl group, a benzyloxymethyl group, a t-butoxymethyl group, a 2-methoxyethoxymethyl group, a 2,2,2-trichloroethoxymethyl group, a bis(2-chloroethoxy)methyl group, a 2-(trimethylsilyl)ethoxymethyl group, a 2-(3-bromotetrahydropyranyl) group, a 2-tetrahydrothiopyranyl group, a 4-(4-methoxytetrahydropyranyl) group, a 4-(4-methoxytetrahydrothiopyranyl) group, a 4-(4-methoxytetrahydrothiopyranyl)-S,S-dioxide group, a 2-tetrahydrofuranyl group, a 1-(1-methyl-1-methoxyethyl) group, or a 1-(1-isopropoxyethyl) group.

6. A process according to claim 1 wherein said first mixture is a mixture of 1-tosyloxy-2-hydroxy-3-butene and 1-tosyloxy-2-acetoxy-3-butene.

7. A process according to claim 6 wherein said volatile compound formed in step (b) is epoxybutadiene.

8. A process according to claim 6 wherein said base used in step (b) is potassium carbonate.

9. A process according to claim 6 wherein said reagent capable of reacting with the alcohol function of said alcohol is dihydropyran.

* * * * *